United States Patent

Stolzenburg et al.

[11] 4,195,992
[45] Apr. 1, 1980

[54] PHOTOGRAPHIC DYE DIFFUSION TRANSFER PROCESS

[75] Inventors: Rudolf Stolzenburg, Duesseldorf; Paul Marx; Walter Puschel, both of Leverkusen, all of Fed. Rep. of Germany

[73] Assignee: Agfa-Gevaert Aktiengesellschaft, Fed. Rep. of Germany

[21] Appl. No.: 925,870

[22] Filed: Jul. 18, 1978

[30] Foreign Application Priority Data

Jul. 22, 1977 [DE] Fed. Rep. of Germany ....... 2733112

[51] Int. Cl.$^2$ .......................... G03C 5/54; G03C 1/40; G03C 1/10
[52] U.S. Cl. .................................... 430/242; 430/223; 430/562
[58] Field of Search ........................ 96/3, 29 D, 77, 99

[56] References Cited

U.S. PATENT DOCUMENTS

| | | | |
|---|---|---|---|
| 3,954,476 | 5/1976 | Krutak et al. | 96/77 |
| 4,013,635 | 3/1977 | Landholm et al. | 96/77 |
| 4,053,312 | 10/1977 | Fleckenstein | 96/77 |
| 4,076,529 | 2/1972 | Fleckenstein et al. | 96/77 |

Primary Examiner—Richard L. Schilling
Attorney, Agent, or Firm—Connolly & Hutz

[57] ABSTRACT

Non-diffusible dye-providing components which may be used in association with a silver halide emulsion layer and on development yield diffusible yellow dyes of improved light fastness are cyanalkyl aminoazo dyes of the formula

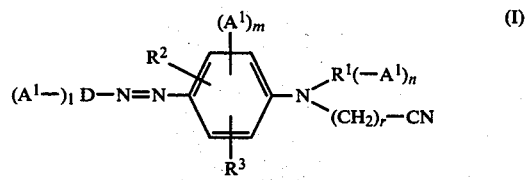

in which
  $A^1$ represents oxidizable carrier residue;
  D represents a heterocyclic or carbocyclic aromatic residue completing an azo dye; and
  l, m and n are 0 or 1 such that $l+m+n=1$;

and r represents an integer of from 1 to 4.

6 Claims, No Drawings

PHOTOGRAPHIC DYE DIFFUSION TRANSFER PROCESS

This invention relates to a process for the preparation of colour photographic images by the dye diffusion transfer process and to a photographic material suitable for this purpose, containing novel diffusion-resistant, dye-providing compounds which release yellow diffusible azo dyes containing a cyanoalkylamino group.

Among the various known processes for the production of coloured photographic images by the dye diffusion transfer process, those which are based on the use of dye-providing compounds which are incorporated in a diffusion resistant form and from which diffusible dyes or dye precursor products are released imagewise in the development process and transferred to an image receiving layer have recently become of increasing importance.

Suitable dye-providing compounds for these processes include, for example, the non-diffusible colour couplers described in German Pat. No. 1,095,115, which, as a result of a reaction with the oxidation product produced by development from a colour developer compound consisting of a primary aromatic amine, release a diffusible dye which is either preformed or produced in the colour coupling reaction. The choise of suitable developer compounds for these colour couplers is, of course, restricted to colour developers.

Other suitable dye-providing compounds include the non-diffusible compounds described in German Offenlegungsschrift No. 1,930,215, in which a preformed dye residue which has a latent capacity for diffusion is linked to a group which confers diffusion resistance through a hydrazone group which can be split. These compounds should not be regarded as colour couplers, and it has in fact been found in this case that the choice of developer compounds, which are necessary for releasing the diffusible dye residue, is by no means limited to the usual colour developers since black-and-white developers, e.g. pyrocatechols, are also very suitable.

Non-diffusible coloured compounds containing a special group which undergo an oxidative ring closure reaction in the development process, thereby releasing a preformed dye residue in a diffusible form, have been described in German Offenlegungsschrist No. 1,772,929. The compounds proposed in the said Offenlegungsschrift may be divided into two groups. The compounds of one group require a conventional colour developer compound for development. They couple with the oxidation product of this colour developer compound and release the preformed dye residue in a diffusible form during a subsequent ring closure reaction. The compounds of the other group are themselves silver halide developers and, in their oxidised form, are therefore capable of entering into the aforesaid ring closure reaction to release the diffusible dyes even in the absence of other developer compounds.

Lastly, the non-diffusible, dye-providing compounds of German Offenlegungsschrift No. 2,242,762 should also be mentioned at this point. These compounds are sulphonamidophenols and sulphonamidoanilines which, after the oxidation which takes place during development, are decomposed under the influence of the developer alkali to release diffusible dyes which carry a free sulphamoyl group.

All the dye-providing compounds mentioned above function negatively, i.e. when conventional, negatively functioning, silver halide emulsions are used, the imagewise distribution of the released diffusible dyes corresponds with the negative silver image produced by development. The production of positive dye images therefore requires the use of direct positive silver halide emulsions or of a suitable reversal process.

In German Offenlegungsschrift Nos. 2,402,900 and 2,543,902, non-diffusible dye-providing compounds have been disclosed which, in their non-oxidized form, are capable of undergoing a splitting reaction under alkaline development conditions to release a diffusible dye but which are imposible or difficult to split when in the oxidized form. Compounds of this type are suitable for use in combination with conventional negative emulsions to produce positive transfer colour images.

Among the known dye-providing compounds, it is difficult to select any which are satisfactory in all respects, both with respect to sufficient reactivity and with regard to sufficient stability. They should not release the diffusible dyes already at the akaline development stage but only after imagewise oxidation by the imagewise developed silver halide has taken place. At the same time, release of the diffusible dyes either from the oxidized or from the non-oxidized dye-providing compounds must take place sufficiently rapidly and the diffusible dyes must also be transferred rapidly.

It is very important that the dyes should be fixed to a sufficient extent in the image receiving layer and that they should have excellent spectral properties and stability to light and heat.

Dye-providing compounds which release yellow dyes for the dye diffusion transfer process have been described in German Offenlegungsschrift No. 2,626,821. These compounds are said to have exceptionally advantageous absorption spectra and excellent colour stability. It was found, however, that the yellow dyes released from these dye-providing compounds leave much to be desired in their stability to light.

It is therefore an object of the present invention to provide new dye-providing compounds for the dye diffusion transfer process, from which diffusible yellow dyes are released during photographic development, which yellow dyes have the desired spectral properties and high resistance to mordants as well as being characterised by improved stability to light.

The present invention relates to a photographic dye diffusion transfer process for the production of coloured images, in which a photographic material comprising at least one light-sensitive silver halide emulsion layer and containing a non-diffusible dye-providing compound associated with this layer is exposed imagewise and developed in the presence of a silver halide developer, and a diffusible dye is released imagewise from the non-diffusible dye-providing compound by the developer, and a diffusible transferred to an image receiving. The process is characterised in that the non-diffusible, dye-providing compound used is a compound corresponding to the following formula

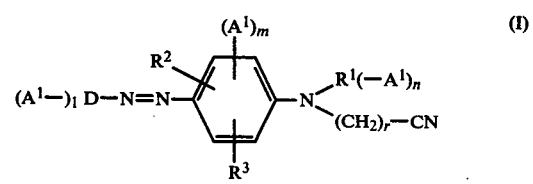

in which $A^1$ represents an oxidizable organic carrier residue containing a group which confers diffusion resistance, from which carrier residue, either in its oxidized or in its unoxidized form, at least part thereof together with the group which confers diffusion resistance is split off under alkaline photographic development conditions, and at the same time a diffusible azo dye is released imagewise;

D represents a heterocyclic or carbocyclic aromatic group preferably a phenyl group;

$R^1$ represents hydrogen, alkyl with 1 to 5 carbon atoms, aralkyl or aryl;

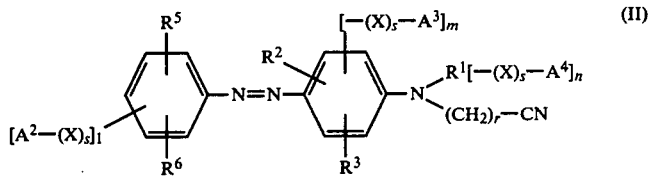

$R^2$ and $R^3$, which may be the same or different, represent one of the groups mentioned under $R^1$, sulpho, —COOR$^4$, halogen, trihalogenmethyl, acylamino, acyloxy, the acyl groups mentioned being derived from aliphatic or aromatic carboxylic or sulphonic acids, including aliphatic and aromatic carbamic acids and carbonic acid monoesters, carbamoyl, sulphamoyl, —OR$^4$, —SR$^4$, —SOR$^4$, —SO$_2$—R$^4$, where R$^4$ has one of the meanings indicated for $R^1$, —NO$_2$ or —CN;

l, m and n each represent 0 or 1 such that $l+m+n=1$;

r represents an integer of from 1 to 4 preferably 2 or 3.

The dye-providing compounds according to the invention thus contain an azo dye residue corresponding to the following formula;

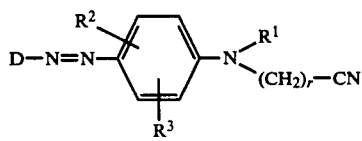

which is attached, either through the group D or through the group $R^1$ or through the benzene ring in the formula, to an oxidizable organic carrier residue which confers diffusion resistance. This carrier residue is such that, either in its oxidized form or in its unoxidized form, it is split off from the dye-providing compounds under alkaline photographic development conditions so that diffusible azo dyes are released. Carrier residues $A^1$ which fulfil such functions are known. Examples include the sulphonamidophenols and slphonamidoanilines described in the above mentioned German Offenlegungsschrift No. 2,242,762, which, after the oxidation which takes place during development, are split by the action of the developer alkali to release diffusible dyes which carry a free sulphonamide group. Other examples include the compounds described in German Offenlegungsschriften Nos. 2,505,248 and 2,654,656,4, e.g. the 3-sulphonamidoindole compounds which have a similar action in that when they are oxidized, they are split by the developer alkali and thereby release diffusible dyes. These compounds therefore also make it possible for dyes to be transferred in the areas where development takes place. German offenlegungsschriften Nos. 2,402,900 and 2,543,902 should also be mentioned at this point. These two Offenlegungsschriften describe dye-providing compounds which, if not oxidized, are split under alkaline development conditions to release diffusible dyes but which are prevented or inhibited from undergoing this splitting reaction when in their oxidized form. Compounds of this type therefore allow dyes to be transferred substantially on in those areas in which no oxidation by development has taken place. They are therefore suitable for the production of positive transfer images.

Compounds used according to the invention which correspond to the following formula II are preferred:

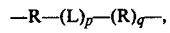

in which $A^2$ represents an oxidizable organic carrier residue in the o-, m- or p-positions to the azo group, which residue may be attached through a connecting member X and contains a group conferring diffusion resistance, from which carrier residue, either in its oxidized form or in its unoxidized form, at least a part thereof, together with the group which confers diffusion resistance, is splitt off under alkaline photographic development conditions a diffusible azo dye being released imagewise at the same time;

$A^3$ represents an oxidizable organic carrier residue containing a group which confers diffusion resistance and which may be attached through a connecting member X, which carrier residue is attached, either directly or through one of the substituents $R^2$ and $R^3$ in the ortho- or meta-position, to the phenyl ring which carries the cyanoalkylamino group, from which carrier residue, either in its oxidized form or in its unoxidized form, at least a part thereof, together with the group which confers diffusion resistance, is split off under alkaline photographic development conditions, a diffusible azo dye being released imagewise at the same time;

$A^4$ represents an oxidizable organic carrier residue containing a group which confers diffusion resistance and which may be attached through a connecting member X, which carrier residue is attached to the substituent $R^1$ and from which, in its oxidized form or its unoxidized form, at least a part thereof, together with the group which confers diffusion resistance, is split off under alkaline photographic development conditions, a diffusible azo dye being released imagewise at the same time;

$R^5$ and $R^6$, which may be the same or different, each represent a substituent of the type defined for $R^2$ and $R^3$ under the definition of formula I, preferably hydrogen,, a halogen such as chlorine, alkyl such as methyl, alkoxy such as methoxy, acylamino such as acetamino, or nitro;

X represents a bivalent connecting member corresponding to the formula $$-R-(L)_p-(R)_q-,$$

in which R represents an alkylene group having from 1 to 6 carbon atoms or a substituted or unsubstituted phenyl group, and the two groups R may be the same or different;

L represents —O—, —CO—, —CONR$^7$, —SO$_2$NR$^7$, —O—CO—NR$^7$, —S—, —SO$_2$— or —SO— in which R$^7$ represents hydrogen or alkyl;

p=0 or 1;

q=0 or 1; and q=1 when p—1 s=0 or 1;

and R$^1$, R$^2$, R$^3$, l, m, n and r have the meanings already indicated.

Compounds used according to the present invention corresponding to the following formula III are particularly preferred:

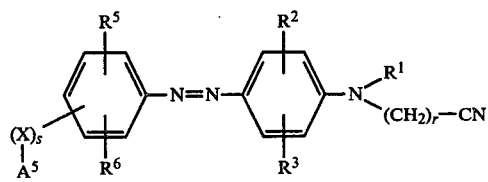

in which the symbols R$^1$, R$^2$, R$^3$, R$^5$, R$^6$, X, r and s have the meanings already specified and A$^5$ represents a residue corresponding to one of the following formulae:

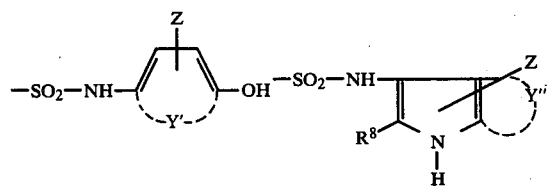

substituted with at least one group which confers diffusion resistance, in which formulae, Z represents a group which confers diffusion resistance, Y' represents a group required to complete a benzene or naphthalene ring, Y" represents the group required to complete a condensed, substituted or unsubstituted carbocyclic or heterocyclic ring, and R$^8$ represents hydrogen, alkyl, alkoxy, aryl, a heterocyclic group, carboxyl, carbamoyl or alkoxycarbonyl.

In the preferred embodiment of the present invention, therefore, A$^5$ together with its linking group —NH—SO$_2$— constitutes a non-diffusible, oxidizable organic carrier residue, moreover one which can only be split by development alkali when it is in its oxidized form. Dye diffusion therefore only occurs in those areas of the photographic material where silver halide development takes place. Dye-providing compounds containing carrier residues of the kind represented by A$^5$ have been described in German Offenlegungsschriften Nos. 2,242,762 2,505,248 and 2,645,656.

The bivalent connecting member X represented in the general formulae II and III may be, for example, a group corresponding to one of the following formulae:

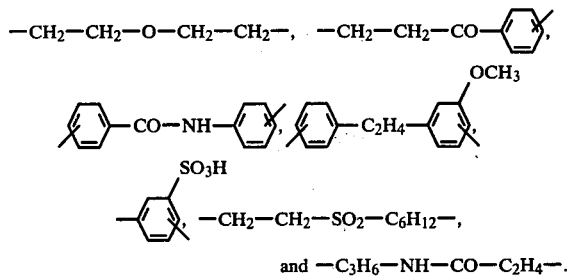

and —C$_3$H$_6$—NH—CO—C$_2$H$_4$—.

It should be pointed out that the dye providing compounds according to this invention should not diffuse through the layers of the photographic material when still intact molecules. They therefore contain a group which confers diffusion resiastance, e.g. the group Z.

The dye-providing compounds may be sufficiently resistant to diffusion even when they do not contain relatively long alkyl groups because the molecule may even then be sufficiently large, depending on the dye residue.

On the other hand, the compounds may be rendered sufficiently resistant to diffusion by choosing sufficiently large residues.

Residues may be regarded as conferring diffusion resistance if they allow the compounds according to the invention to be incorporated in a diffusion-fast form in the hydrophilic colloids normally used in photographic materials. Particularly suitable for this purpose are organic residues generally containing straight or branched chain aliphatic group, which may also contain carbocyclic of heterocyclic groups, generally having from 8 to 20 carbon atoms. These residues are attached to the remainder of the molecule either directly or indirectly, e.g. through one of the following groups: —NHCO—, —NHSO$_2$—, —NR—, where R represents hydrogen or alkyl; —O— or —S—. The residue which confers diffusion resistance may also contain water-solubilizing groups, e.g. sulpho or carboxyl groups, and these may also be present in an anionic form. Since the diffusion properties depend on the molecular size of the compound as a whole, it is in some cases sufficient, for example if the whole molecule is large enough, to use relatively short chain residues for conferring diffusion resistance.

When development takes place, at least part of the carrier residue, together with the group which confers diffusion resistance, is split off from the non-diffusible dye-providing compounds according to the invention and at the same time a diffusible azo dye is released. A chemical change may at the same time take place in the carrier residue which has been split off, e.g. an intramolecular rearrangement such as a ring closure reaction.

In the case of the non-diffusible dye-providing compounds corresponding to formula III, for example, the released diffusible azo dyes contain a free sulphamoyl group and correspond to the following formula IV:

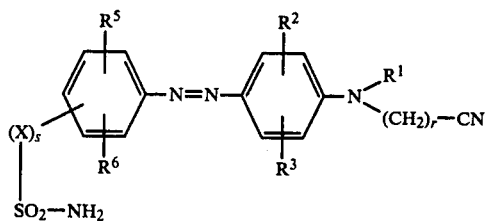

in which $R^1$, $R^2$, $R^3$, $R^5$, $R^6$ r and s have the meaning already indicated.

The following examples of suitable dye providing compounds according to the present invention:

$A^6 =$

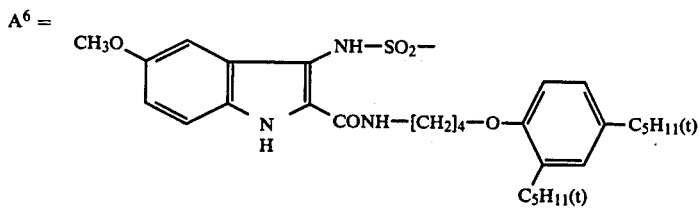

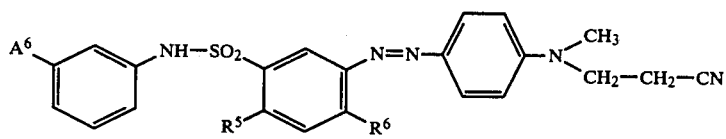

| Compound No. | $R^5$ | $R^6$ | $\lambda_{max}$ [nm] |
|---|---|---|---|
| 1 | H | H | 424 |
| 2 | H | Cl | 436 |
| 3 | H | $CH_3$ | 423 |
| 4 | H | $OCH_3$ | 426 |
| 5 | Cl | H | 430 |
| 6 | $CH_3$ | H | 417 |

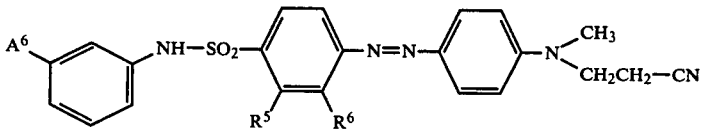

| Compound No. | $R^5$ | $R^6$ | $\lambda_{max}$ [nm] |
|---|---|---|---|
| 7 | H | H | 431 |
| 8 | Cl | H | 447 |
| 9 | $CH_3$ | H | 433 |

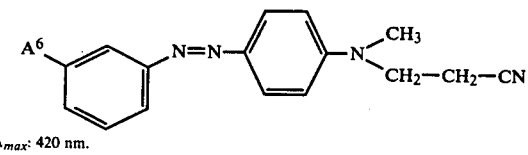

$\lambda_{max}$: 420 nm.

Preparation of Compound No. 2

(a) 3-(4-N-Methyl-N-cyanoethyl-aminobenzene-azo)-4-chlorobenzene sulphonic acid

A solution of 20.7 g of sodium nitrite in 60 ml of water was added dropwise at 0° to 5° C. to a suspension of 69.2 g of 3-amino-4-chlorobenzene sulphonic acid (90%) in 500 ml of water and 90 ml of concentrated hydrochloric acid. The suspension was then stirred for 30 minutes. Excess nitrite was destroyed with amidosulphonic acid. The suspension was introduced at 5° to 10° C. into a solution of 48 g of 3-(N-methyl-anilino)-propionic acid nitrile in 240 ml of acetone. The pH was then adjusted to 3.5 with 20% sodium acetate solution. The reaction mixture was stirred for 3 hours at 5° to 10° C. and then overnight without cooling. The dye was isolated by suction filtration, washed with 10% sodium chloride solution and dried. Yield: 93 g; Mp.: >225° C. (decomposition).

(b) 3-(4-N-Methyl-N-cyanoethyl-aminobenzene-azo)-4-chlorobenzene sulphonic acid chloride 22.8 ml of $POCl_3$ were added to 140 ml of dimethyl formamide. The solution was cooled to 25° C. and 19 g of 3-(4-N-methyl-N-cyanoethyl-amonobenzene-azo)-4-chlorobenzene sulphonic acid were added at 25° C. The reaction mixturewas then stirred for one hour at 25° C.

and poured on to ice. The resulting precipitate was suction filtered, washed with water and dried. Yield: 18 g; Mp.: >155° C. (decomposition).

(c) Compound No. 2.

6.48 g of the compound corresponding to the following formula:

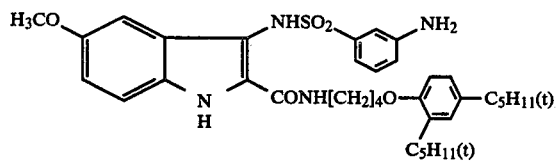

which had been prepared by the reaction of 2-(2,4-ditert.-pentylphenoxybutylamino-carbonyl)-3-amino-5-methoxy-indole, prepared by one of the methods described in German Patent Offenlegungsschrift 2,645,656, with 3-nitrobenzene sulphonic acid chloride followed by catalytic hydrogenation was stirred up into a slurry with 100 ml of chloroform and 3.2 ml of pyridine, and to the resulting mixture were added 4.4 g of 3-(N-methyl-N-cyanoethyl-aminobenzene-azo)-4-chlorobenzene sulphonic acid chloride. The reaction mixture was stirred for 10 hours at 40° C. It was then cooled and stirred for 30 minutes with the addition of 350 ml of methanol. The resulting precipitate was suction filtered, washed with methanol and dried. Yield: 6.1 g; M.p.: 244°–246° C. (decomposition).

The other dye-providing compounds according to the present invention may be prepared by similar methods.

The diffusible dyes split off from the dye providing compounds according to the invention were used for measuring the absorption and fastness to light (see Example 2). As example, there will now be described the preparation of the dye released from compound 22.

Dye of Compound 2:

1.73 g of 3-aminobenzene sulphonic acid amide were stirred up in 40 ml of chloroform and 3.2 ml of pyridine, and to this mixture were added 4.4 g of 3-(4-N-methyl-N-cyanyoethyl-aminobenzene-azo)-4-chlorobenzene sulphonic acid chloride (90%). The reaction mixture was then stirred for 4 hours at 40° C. A further 0.4 g of sulphochloride was added and the mixture again stirred at 40° C. for 3 hours. The resulting precipitate was suction filtered, washed with chloroform and dried. The filter cake was stirred up with 2N-hydrochloric acid, suction filtered and washed with 2N-hydrochloric acid and water. The substance was then purified by repeated extraction with ethyl acetate and concentration of the mother liquor. Yield: 3.5; M.p.: 120°–122° C. (decomposition).

The compounds according to the invention are yellow. They are incorporated in the casting solutions for the layers of photographic material by one of the usual methods. The quantity of dye-providing compounds used per liter of casting solution varies within relatively wide limits, the most sitable concentration being determined by the aid of simple tests. For example, from 5 to 80 g, preferably from 20 to 40 g of dye-providing compound may be used per liter of casting solution.

The association between diffusion resistant dye-providing compounds and silver halide, which is necessary to obtain the desired effect, may be established, for example, by introducing the diffusion resistant compound into the casting solution from aqueous alkaline solutions, making use of the water-solubilizing groups present. Alternatively, the non-diffusible dye-providing compound may be incorporated in the layers by one of the known emulsification processes. Such processes have been described, for example, in British Pat. Nos. 791,219 and 1,099,414 to 1,099,417. Another method consists of preparing aqueous dispersion of the dye-providing compounds and then adding them to the casting solutions. For this purpose, aqueous slurries of the dye-providing compound are finely milled, for example by vigerous stirring with the addition of sharp edges sand or by means of ultra-sound. In other cases, it may be desirable, for example, to incorporate the dye-providing compounds in the layer in the form of so-called microcapsules together with silver halide and optionally developer substances. In such cases, two or more differently sensitized light-sensitive silver halide emulsions and the corresponding diffusion resistant compounds may be combined in a single layer in the form of so-called mixed grain emulsions, for example as described in U.S. Pat. No. 2,698,794. The non-diffusible dye-providing compounds may be incorporated in a light-sensitive layer or in an adjacent layer. For example, a compound which releases a cyan dye may be associated with the red-sensitive layer, a compound releasing a magenta dye with the green-sensitive layer and a compound according to the invention which releases a yellow dye may be associated with the blue sensitive layer.

By "association" and "associated" is meant that the silver halide emulsion and the dye-providing compound are so arranged in relation to each other that interaction between them may take place to result in an imagewise correspondence between the silver image, in the case of negatively functioning dye-providing compounds or undeveloped silver halide, in the case of positively functioning dye-providing compounds on the one hand and the imagewise distribution of the released diffusible dye on the other. For this purpose, the associated dye-providing compound may be incorporated in the silver halide emulsion itself or in a layer adjacent to this silver halide emulsion layer, which adjacent layer is preferably situated behind the silver halide emulsion layer, viewed in the direction of the incident light used for exposure. Development of the silver image causes the dye-providing compounds according to the invention to be oxidized imagewise by oxidation products of the developer, and they are then subjected to a splitting reaction under the alkaline photographic development condition for example by the alkali of the developer or of the activator, whereby the dye residues are released in a diffusible form, generally as dye sulphonamides. The usual photographic developer compounds are suitable for this development, provided that they are capable, when in their oxidized form, of oxidizing the dye-providing compounds according to the invention. The following are examples of suitable developers:
Hydroquinone,
N-methylaminophenol,
1-phenyl-3-pyrazolidone,
1-phenyl-4,4-dimethyl-3-pyrazolidone, 1-phenyl-4-methyl-4-hydroxymethyl-3-pyrazolidone,
aminophenols,
N,N-diethyl-p-phenylenediamine,
N-ethyl-N-hydroxyethyl-p-phenylene diamine,
N-ethyl-N-ω-sulphobutyl-p-phenylenediamine,
3-methyl-N,N-diethyl-p-phenylendiamine, N,N,N',N'-tetraalkyl-p-phenylenediamines such as tetramethyl-p-phenylenediamine or 1,4-bis-pyrrolidinobenzene, and reductones.

It should be particularly mentioned that the choice of developer substances used in the process according to the invention is not limited to colour developers but that conventional black-and-white developers may also be used, which is an advantage in view of the smaller risk of discoloration of the latter. The developers may be contained in the layers of colour photographic material, where they are activated by the alkaline activator liquid, or they may be contained in the alkaline processing liquid or paste. Since the dye-providing compounds according to the invention have developer properties, the use of auxiliary developer compounds may in some cases be dispensed with. In such cases, the dye-providing compound is directly oxidized by the developable silver halide.

If the imagewise distribution of the diffusible dye released by development corresponds with the developed silver image, as is the case with dye-providing compounds of the type described in German Offenlegungsschriften Nos. 2,242,762; 2,505,248 and 1,772,929, direct positive silver halide emulsions are required for producing positive coloured transfer images or, if conventional negative emulsions are used, a suitable reversal process is required. In the case of the dye-providing compounds described in the last mentioned German Offenlegungsschrift, the diffusible dyes are released not as a direct result of being split by alkali but rather as a result of an intramolecular displacement reaction accompanied by ring closure. Moreover, the released dyes do not carry a free sulphamoyl group as do the dyes released from the preferred dye-providing compounds according to this invention but a sulphinic acid group. However, the invention is by no means restricted to those dye-providing compounds which are split directly by alkalies.

A suitable reversal process of this kind is the silver salt diffusion process. Photographic reversal by the silver salt diffusion process to produce positive coloured images with the aid of conventional colour couplers has been described, for example, in U.S. Pat. No. 2,763,800. A light-sensitive element suitable for the dye diffusion transfer process is obtained by exchanging the colour couplers for the above-mentioned dye-providing compounds. A light-sensitive element of this kind may comprise, for example, at least one combination of a light sensitive silver halide emulsion layer and a layer of binder which is associated with this silver halide emulsion layer and contains development nuclei for physical development and a dye-providing compound.

When development takes place, the exposed part of the silver halide in the light-sensitive silver halide emulsion layer is developed chemically. The unexposed part is transferred to the associated layer of binder which contains development nuclei by means of a silver halide solvent, and is physically developed there. If the developer used for physical development is one which, in its oxidized form, is capable of releasing a diffusible dye as a result of a reaction with the dye-providing compound present in this layer, then an imagewise distribution of diffusible dyes is obtained, which may be transferred to an image receiving layer to produce a positive coloured image there.

When reversal is carried out using compounds which release development inhibitors in imagewise distribution, the light-sensitive element consists of at least one layer combination of a light-sensitive silver halide emulsion layer and a second emulsion layer which contains the dye-providing compound and is developable without exposure. The light-sensitive silver halide emulsion layer is developed, for example, with colour developers, in the presence of certain compounds which react with oxidized colour developer to release development inhibiting substances. The development inhibiting substances released imagewise in the light-sensitive layer diffuse into the adjacent emulsion layer which is developable without exposure, and inhibit imagewise development in this layer. The uninhibited (positive) parts of this emulsion layer which is developable without exposure are developed by the residual developer, whose oxidation products then react with the non-diffusible dye-providing compounds according to the invention to release diffusible dyes which are transferred imagewise to the image receiving element. Suitable compounds which release development inhibiting substances in their reaction with developer oxidation products include, for example the known DIR couplers (DIR = development inhibitor releasing) which are colour couplers containing a releasable inhibitor group in the coupling position. DIR couplers of this type have been described, for example in U.S. Pat. No. 3,227,554.

Another group of compounds which release development inhibiting substances in their reaction with colour developer oxidation products has been described in U.S. Pat. No. 3,632,345. These compounds are not colour couplers and no dyes are therefore formed when the development inhibiting substances are released. Lastly, according to German Pat. No. 1,229,389, suitable substituted, non-diffusible hydroquinone compounds which are oxidized to the corresponding quinones by their reaction with developer oxidation products and thereby split off development inhibiting mercaptans may also be used in such a process.

The direct positive silver halide emulsions used may, in principle be any direct positive silver halide emulsions which produce a positive silver image and a corresponding imagewise distribution of developer oxidation products by a simple development process. They include, for example, those silver halide emulsions in which exposure or chemical treatment has produced a developable fog which, under certain conditions, is destroyed imagewise by imagewise exposure of the film. A fog remains in the unexposed areas, so that when the material is subsequently developed, a direct positive silver image is obtained and, corresponding therewith, an imagewise distribution of diffusible dye if a dye-providing compound according to the invention has been associated with the direct positive silver halide emulsion.

Another group of direct positive silver halide emulsions which are preferred according to the present invention comprises the so-called unfogged direct positive silver halide emulsions in which the sensitivity to light resides mainly in the interior of the silver halide grains. When such emulsions are exposed imagewise, a latent image is formed predominantly in the interior of the silver halide grains. The development of such unfogged direct positive silver halide emulsions is carried out under fogging conditions so that a fog is produced mainly in the unexposed areas and development results in a positive silver image. Unfogged direct positive silver halide emulsions are characterised in that, when unexposed samples are developed with a typical surface developer of the following composition:

| | |
|---|---|
| p-Hydroxyphenylglycine | 10 g |
| sodium carbonate (crystallised) | 100 g |
| made up with water to | 1000 ml | they preferably do not produce a silver image or only one of very low density whereas a sufficiently dense silver image is obtained when an internal nuclear developer of the following composition is used:

| | |
|---|---|
| Hydroquinone | 15 g |
| Monomethyl-p-aminophenolsulphate | 15 g |
| Sodium sulphite (anhydrous) | 50 g |
| Potassium bromide | 10 g |
| Sodium hydroxide | 25 g |
| Sodium thiosulphate (crystallised) | 20 g |
| made up with water to | 1000 ml. |

Selective fogging of unfogged direct positive emulsions which have been exposed imagewise may be carried out by treatment with a fogging agent either before or during development. Reducing agents such as hydrazine or substituted hydrazines are suitable fogging agents. Reference may be found, for example, in U.S. Pat. No. 3,227,552; the fogging agent may also be incorporated in a diffusion resistant form.

Unfogged direct positive emulsions include, for example, those which have deficiencies in the interior of the silver halide grains as described in U.S. Pat. No. 2,592,250, or silver halide emulsions which have a layered grain structure (as described in German Offenlegungsschrift No. 2,308,239).

If the dye-providing compounds according to the invention contain a non-diffusible oxidizable carrier group of the type described in German Offenlegungsschriften Nos. 2,402,900 and 2,543,902, i.e. a carrier residue which can only be split off by alkali so long as it is in its unoxidized form but is difficult or impossible to split off when oxidized, it is, of course, not necessary to use direct positive emulsions or a reversal process for producing positive transfer images but only a conventional negative emulsion.

The emulsions may also be chemically sensitized, for example by the addition of sulphur compounds such as allyl isothiocyanate, allylthiourea and sodium thiosulphate at the chemical ripening stage. Reducing agents may also be used as chemical sensitizers, for example, the tin compounds described in Belgian Pat. Nos. 493,464 and 568,687, polyamines such as diethylene triamine or aminomethane sulphinic acid derivatives, e.g. according to Belgian Pat. No. 547,323.

Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 46, 65–72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols or cyclic dehydration products of hexitols, or with alkyl substituted phenols, aliphatic carboxylic acids, aliphatic amines, aliphatic diamines and amides. The condensation products should have a molecular weight of at least 700, preferably more than 1000. These sensitizers may, of course, be combined in order to produce special effects, as described in Belgian Pat. No. 537,278 and British Pat. No. 727,982.

The emulsions may also be spectrally sensitized, e.g. with the usual monomethine or polymethine dyes such as acid or basic cyanines, hemicyanines, streptocyanines, merocyananines, oxonoles, hemioxonones or styryl dyes or trinuclear or higher nuclear methine dyes, for example rhodacyanines or neocyanines. Sensitizers of this type have been described, for example, in the work by F. M. Hamer "The Cyanine Dyes and Related Compounds" (1964) Interscience Publishers John Wiley and Sons.

The emulsions may also contain the usual stabilizers, e.g. homopolar compounds or salt compounds of mercury containing aromatic or heterocyclic rings, such as mercaptotriazoles, or simple mercury salts, sulphonium mercury double salts and other mercury compounds. Azaindenes are also suitable stabilizers, particularly the tetra- and penta-azaindenes and especially those which are substituted with hydroxyl or amino groups. Compounds of this type have been described in the article by Birr, Z. Wiss. Phot. 47, 2–27 (1952). Other suitable stabilizers include, inter alia, heterocyclic mercapto compounds, e.g. phenylmercaptotetrazole, quaternary benzothiazole derivatives and benzotriazole.

The binder used for the photographic layers is preferably gelatine although this may be partly or completely replaced by other natural or synthetic binders. Suitable natural binders include e.g. alginic acid and its derivatives such as its salts, esters or amides, cellulose derivatives such as carboxymethylcellulose, alkylcelluloses such as hydroxyethylcellulose, starch and its derivatives such as its ethers or esters or carrageenates. Suitable synthetic binders include polyvinyl alcohol, partially saponified polyvinyl acetate and polyvinylpyrrolidone.

The layers may be hardened by the usual methods, for example with formaldehyde or halogen substituted aldehydes which contain a carboxyl group, such as mucobromoic acid, diketones, methane sulphonic acid esters or dialdehydes.

To carry out the dye diffusion transfer process according to the present invention, a light-sensitive element is used which contains one or more silver halide emulsion layers as well as non-diffusible, dye-providing compounds associated with these layers, and an image receiving element in which the desired colour image is produced by the diffusible dyes which have been transferred imagewise. To effect this transfer, firm contact must be established between the light-sensitive element and the image receiving element for at least a finite length of time during the period of development, so that the imagewise distribution of diffusible dyes produced by development in the light-sensitive element can be transferred to the image receiving element. This contact may be established after development has been started or it may even be established before the onset of development. The latter would be the case if, for example, the material used for carrying out the dye diffusion transfer process is one in which the light-sensitive element and the image receiving element form an integral unit, hereinafter also referred to as monosheet material, which is left intact even after development, i.e. the light-sensitive element is not separated from the image receiving element even after transfer of the dyes. Such an embodiment has been described in, for example, German Offenlegungsschrift No. 2,019,430.

A monosheet material suitable for carrying out the dye diffusion transfer process according to the present invention may comprise, for example, the following layer elements:

(1) a transparent substrate layer
(2) an image receiving layer
(3) a light impervious layer
(4) a light-sensitive element having at least one light-sensitive silver halide emulsion layer and at least one non-diffusible dye providing compound associated with this layer,
(5) a retarding layer,
(6) an acid polymer layer,
(7) a transparent substrate layer.

The elements of the monosheet material may be arranged so that two different parts are prepared separately from each other, namely the light-sensitive part (layer elements 1 to 4) and the cover sheet (layer elements 5 to 7), these two parts being then placed together with their active surfaces in contact and bonded together, optionally with the interposition of spacer strips so that a space is left between the two parts for an accurately calculated quantity of processing liquid. The layer elements 5 and 6, which together form the neutralisation system, may also be arranged between the substrate layer and the image receiving layer of the light-sensitive part, but in this case their sequence would be reversed.

Means may be provided for introducing a processing liquid between the light-sensitive part and the cover sheet, for example in the form of an rupturable container arranged at the side of the material so that it pours out its contents between two adjacent layers of the monosheet material when subjected to mechanical forces.

An essential part of the photographic material according to the present invention is the light-sensitive element which, in the case of a single-dye transfer process, contains a light-sensitive silver halide emulsion layer and a non-diffusible dye-providing compound associated therewith. This non-diffusible compound may be situated in a layer adjacent to the silver halide emulsion layer or in the silver halide emulsion layer itself. In the latter case, the colour of the image dye is preferably chosen so that the predominant absorption range of the dye-providing compound does not correspond with the predominant sensitivity range of the silver halide emulsion layer.

To produce multicoloured transfer images in true-to-life colours, the light-sensitive element contains three such associations of dye-providing compound in light-sensitive silver halide emulsion layer, and the general substantially corresponds to the range of spectral sensitivity of the associated silver halide emulsion layer. In that case, in order to obtain the highest possible sensitivity it is necessary that the dye providing combination should be arranged in a separate layer of binder behind, viewed in the direction of incident light during exposure, the silver halide emulsion layer.

The action of the developer oxidation products produced by development of the silver halide emulsion must, of course be restricted to the associated dye-providing compounds. Separating layers are therefore generally provided in the light-sensitive element to prevent diffusion of the developer oxidation products into other layers with which they are not associated. These separating layers may, for example, contain suitable substances which react with the developer oxidation products, for example, non-diffusible hydroquinone derivatives or, if the developer is a colour developer substance, non-diffusible colour couplers. In a preferred arrangement, therefore, the light-sensitive element has the following arrangement of components (from below upwards):

blue sensitive silver halide emulsion layer,
layer containing non-diffusible compound which releases a diffusible yellow dye,
separating layer,
green sensitized silver halide emulsion layer,
layer containing non-diffusible compound which releases a diffusible magenta dye,
separating layer,
red-sensitized silver halide emulsion layer,
layer containing non-diffusible compound which releases a diffusible cyan dye.

The silver halide emulsion layers may, of course, also be arranged in a different sequence, but in that case the associated layers must also be interchanged with the dye-providing system so that the association is preserved.

The light-impervious layer arranged under the light-sensitive element is permeable to aqueous alkaline treatment solutions and hence to diffusible dyes. It has two main functions: first, it serves to cover the image silver left in the originally light-sensitive element after development as well as the dye-providing compounds left behind as colour negative so that when the photographic material is viewed through the transparent support layer of the light-sensitive part, only the positive transfer image is visible; second, it provides a light-proof cover for the light-sensitive element on the side facing the image receiving layer (from below). The latter is particularly important in cases where the monosheet material is brought into contact with the alkaline processing mass while still in the camera after exposure and is then to be pulled ejected.

Layers which are sufficiently impervious to light but sufficiently permeable to diffusible dyes may be prepared, for example, from suspension of inorganic or organic dark pigments, preferably black pigments, for example suspensions of carbon black, in suitable binders, e.g. in gelatine solutions. To ensure adequate exclusion of light during development, it is generally sufficient to use layers from 0.5 to 2 $\mu$ in thickness containing from 10 to 90% by weight, based on the total dry weight, of carbon black in gelatine. The particle size of the pigment used is relatively uncritical, provided that it is not substantially above 0.5 $\mu$.

In addition to the black pigment layer, the light impervious layer preferably also includes a white pigment layer arranged underneath it. The purpose of this white pigment layer is to cover the black layer and to provide a white background for the image. Any white pigments are suitable for this layer, provided it is not necessary to use unduly thick layers to obtain the necessary covering power. Examples of such pigments include barium sulphate, oxides of zinc, titanium, silicon, aluminium and zirconium, barium stearate and kaolin. The white pigment which is preferably used is titanium dioxide. The same conditions apply with regard to the binder, concentration and particle size as for the black pigments. The thickness of the white pigment layer may be varied according to the desired degree of whiteness of the background. Thicknesses of between 5 and 20 $\mu$ are preferred.

Instead of containing a light impervious layer, the monosheet material according to the present invention may contain means for producing such a layer between the light-sensitive element and the image receiving layer, for example in the form of a container for a liquid containing a clouding agent (pigment) arranged at the side of the monosheet material so that it releases its contents between the above mentioned layers when exposed to mechanical forces, to form such a pigment layer between them.

The image receiving layer consists basically of a binder containing dye mordants for fixing the diffusible dyes.

The mordants used for acid dyes are preferably long chain quaternary ammonium or phosphonium compounds or ternary sulphonium compounds, e.g. those described in U.S. Pat. Nos. 3,271,147 and 3,271,148. Certain metal salts and their hydroxides which react with acid dyes to form sparingly soluble compounds may also be used. The dye mordants are dispersed in the receiving layer in one of the usual hydrophilic binders, e.g. in gelatine, polyvinyl pyrrolidone or partially or completely hydrolysed cellulose esters. Some binders may, of course, themselves function as mordants, e.g. copolymers or polymer mixtures of vinyl alcohol and N-vinylpyrrolidone, for example as described in German Auslegeschrift No. 1,130,284, or binders which consist of polymers of quaternary nitrogen bases, e.g. polymers of N-methyl-2-vinylpyridine, for example, as described in U.S. Pat. No. 2,484,430. Guanyl hydrazone derivatives of acyl styrene polymers such as those described in German Offenlegungsschrift No. 2,009,498, for example, are also binders which function as mordants. However, the last mentioned mordanting binders would generally be used in combination with other binders, e.g. gelatine.

The usual transparent substrate materials used in photographic practice may be used as transparent substrate layers for the monosheet material according to the invention, e.g. films of cellulose esters, polyethylene terephthalate, polycarbonates or other film forming polymers.

The alkaline processing substance adjusts the light sensitive material to a relatively high pH, about 11 to 14, which releases development and imagewise dye diffusion. It has been found that the dyes, and hence the images obtained, are not particularly stable at such high pH values. It is therefore necessary to adjust the material to almost neutral or slightly acid after development has been completed. This can be achieved in known manner by providing the material with an additional acid polymer layer which becomes accessible to the alkaline processing substance only gradually during development. By "acid polymer layer" is meant a layer of binder containing polymeric compounds which have acid groups, preferably sulpho or carboxyl groups. These acid groups react with the cations of the processing substance to form salts, thereby lowering the pH of the substance. The polymer compounds and hence the acid groups are, of course, incorporated in a diffusion resistant form in the said layer. The acid polymers are in many cases derivatives of cellulose or derivatives of polyvinyl compounds, but other polymer compounds may also be used. The following are mentioned as examples of suitable acid polymers: Cellulose derivatives having a free carboxyl group, e.g. cellulose dicarboxylic acid semiesters with a free carboxyl group, such as cellulose acetate hydrogen phthalate, cellulose acetae hydrogen glutarate, ethyl cellulose acetate hydrogen succinate, cellulose acetate hydrogen succinate hydrogen phthalate, ethers and esters of cellulose which have been modified with other dicarboxylic acid anhydrides or with sulphonic acid anhydrides, for example with o-sulphobenzoic acid anhydride; carboxymethylcellulose; polystyrene sulphonic acid; polyvinylhydrogenphthalate; polyvinylacetatehydrogenphthalate; polyacrylic acid; acetals of polyvinyl alcohol with aldehydes which are substituted with carboxyl or sulpho groups, such as o-, m- or p-benzaldehyde sulphonic or carboxylic acid, partially esterified ethylene/maleic acid anhydride copolymers and partially esterified methyl vinyl ether/maleic acid anhydride copolymers.

The acid polymer layer must contain sufficient acid groups to lower the pH of the processing substance from an initial value of 11 to 14 so that the material will finally be almost neutral or slightly acid (pH 5 to 8).

The time delay in lowering of the pH is achieved in known manner by coating the acid polymer layer with a so-called retarding layer. This retarding layer is an alkali impermeable layer preferably consisting of a polymer which is inert to alkalides, for example a polyvinyl alcohol or a partially acetalised polyvinyl alcohol. The amount of delay in lowering of the pH can be adjusted as desired by a suitable choice of the thickness and composition of this retarding layer. A barrier layer containing polymers having a new type of permeability behaviour has been described, for example, in German Offenlegungsschrift No. 2,455,762.

Neutralisation systems, that is to say, combinations of an acid polymer layer and a retarding layer, have been described, for example in German Pat. No. 1,285,310. Layer combinations of this type may be provided in the material according to the invention, for example in the light-sensitive part, between the transparent layer substrate and the image receiving layer.

Another possible arrangement consists of placing the neutralisation system consisting of acid polymer layer and retarding layer on the cover sheet. The two layers must, of course, be arranged in such a sequence that the alkali of the processing substance must penetrate the retarding layer before it can reach the acid polymer layer.

The dye diffusion transfer process according to the invention may advantageously be carried out in or with a suitable self-developing camera. This camera may be provided, for example, with devices which make it possible for a solution to be distributed between the light-sensitive element and the cover sheet after exposure of the light-sensitive element, this solution serving to shield the light-sensitive material against light from above. A camera of this kind is preferably equipped with a pair of squeezing rollers between which the monosheet material is pulled out so that the containers arranged at the side of the monosheet material are split open in their passage between the rollers and release their contents between the layers of the monosheet material.

Since the light-sensitive element is protected against unwanted exposure on both sides by light impervious layers after it has passed between the squeezing rollers, the exposed material may be pulled out of the camera as soon as development has been started.

To process the monosheet material after it has been exposed imagewise, the light-sensitive element is brought into contact with the aqueous alkaline processing solution. The silver halide emulsion layers which have been exposed imagewise are thereby developed in the presence of the developer compound, and an imagewise distribution of oxidation products of the developer compound is obtained in correspondence with the silver image produced by development, the said oxidation products of the developer compound oxidizing the associated dye-providing compound, whereupon the oxidized dye-providing compound reacts with the alkali of the activator or developer, thereby releasing the diffusible dye.

The aqueous alkaline processing solution may contain viscosity increasing additives, e.g. hydroxyethylcellulose. It may also contain the usual development accelerators, stabilizers, silver salt solvents, fogging agents or antioxidants and other additives.

EXAMPLE 1

A light-sensitive element of a photographic material according to the invention was prepared by applying the following layers one after the other to a transparent polyester foil serving as substrate. The quantities given are based in each case on 1 m².

(1) A mordant layer of 6 g of a polyurethane of 4,4-diphenylmethane diisocyanate, N-ethyldiethanolamine and epichlorohydrin and 6.0 g of gelatine.

(2) A reflection layer of 24 g of titanium dioxide and 2.4 g of gelatine.

(3) A carbon black layer of 1.9 g of carbon black and 2 g of gelatine.

(4) A dye layer of 0.5 g of compound I (cyan) and 0.9 g of gelaine.

(5) A red sensitized emulsion layer containing an unfogged direct positively functioning silver chlorobromide emulsion, silver application 2,6 g, gelatine 1.3 g and 0.04 g of N-[α-(2.4-ditert.-amyl-phenoxy)-acetyl]-N'-phenyl-hydrazine as fogging agent.

(6) A barrier layer of 0.5 g of octadecylhydroquinone sulphonic acid and 1.3 g of gelatine.

(7) A dye layer of 0.5 g of compound II (magenta) and 0.9 g of gelatine.

(8) A green sensitized emulsion layer containing an unfogged direct positively functioning silver chlorobromide emulsion, silver application 2.5 g, gelatine 1.28 g and 0.04 g of N-[α-(2.4-ditert.-amyl-phenoxy)-acetyl]-N'-phenyl-hydrazine as fogging agent.

(9) A barrier layer identical to layer (6).

(10) A dye layer of 0.65 g of compound III (yellow) and 1.0 g of gelatine.

(11) A blue sensitized emulsion layer containing an unfogged direct positively functioning silver chlorobromide emulsion, silver application 2.7 g, gelatine 1.4 g. and 0.04 g of N-[α-(2,4-ditert.-amyl-phenoxy)-acetyl]-N'-phenyl-hydrazine as fogging agent.

(12) A protective layer of 0.8 g of gelatine and 0.8 g of a compound corresponding to the following formula (hardener):

$$C_2H_5-N=C=N-CH_2-CH_2-CH_2-\overset{\oplus}{N}(C_2H_5)_3 \quad Cl^{\ominus}$$

(13) A transparent cover sheet of polyethylene terephthalate with a neutralisation layer and a retarding layer.

After exposure through a step wedge, the light-sensitive element was covered with the transparent cover sheet on the side on which the active layer was exposed. A rupturable container containing an alkaline processing liquid of the following composition was used for developing the light-sensitive element after imagewise exposure:

50 g potassium hydroxide;

10 ml benzyl alcohol;

3 g benzotriazole;

1 g sodium sulphite;

6.0 g 1-phenyl-4-methyl-4-hydroxymethyl-3-pyrazolidone 0.1 g hydroquinone;

34 g hydroxyethylcellulose made up with water to 1000 ml.

The film set was passed through a pair of squeezing rollers to distribute the developer paste between the light-sensitive element and the cover sheet. The thickness of the layer of paste was 110 μ. To adjust this thickness, spacer strips of the appropriate thickness were placed laterally along the edge of the image, between the light-sensitive element and the cover sheet.

Other light-sensitive elements were prepared in the same way except that dye III of the layer was replaced by one of the compounds according to the invention Nos. 3 to 7. After the same method of processing, direct positive multicoloured copies of the original were again obtained (Filmsets B-F).

After development time of 1 hour, the $D_{max}$ and $D_{min}$ values of the image receiving layers given in the following Table were obtained by means of a reflection densitometer using a blue filter.

Table

| Filmset | Compound | $D_{max}$ | $D_{min}$ |
|---------|----------|-----------|-----------|
| A | III | 1.65 | 0.32 |
| B | 3 | 1.70 | 0.29 |
| C | 4 | 1.52 | 0.32 |
| C | 5 | 1.92 | 0.31 |
| E | 6 | 1.71 | 0.29 |
| F | 7 | 1.98 | 0.30 |

The results show that the dye-providing compounds according to the present invention make it possible for higher transfer colour densities to be obtained. Annexe of formulae to Example 1.

cyan (I)

magenta (II)

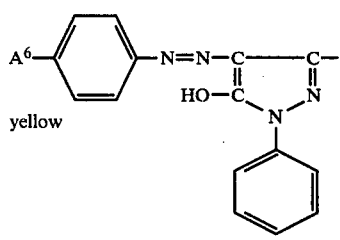

yellow

EXAMPLE 2

The lightfastness and absorption were measured on the transfer dyes which had been released in a diffusible form from the dye-providing compounds.

The dye which was to be tested was mordanted by continuous immersion of a transparent support layer containing a mordant layer corresponding to layer 1 from Example 1 in an aqueous dye solution, followed by 2 minutes washing and drying.

The absorption measurements were carried out with a spectral photometer.

To test the lightfastness, one strip of each of the resulting materials containing the dyes which are to be compared was fixed to a titanium dioxide support and exposed to $1.10^5$ lx for 24 hours (ca. 20° C., ca. 60% relative humidity) in a Xenotest apparatus of Hanau. The residual density after such exposure was calculated according to the following equation:

$$\text{Residual density} = \frac{\text{Colour density after exposure}}{\text{Colour density before exposure}} \cdot 100(\%)$$

Measurement was carried out within the density range (before exposure) of from 1.0 to 1.5.

The residual densities obtained are shown in the following Table.

Table

| Dye from Compound | Residual density [%] |
|---|---|
| 1 | 63 |
| 2 | 69 |
| 3 | 74 |
| 4 | 78 |
| 5 | 70 |
| 6 | 67 |
| 7 | 77 |
| 8 | 71 |
| 9 | 75 |
| 10 | 75 |
| III (Comparison) | 34 |

We claim:

1. Photographic dye diffusion transfer process for the production of coloured images, in which a photographic material having at least one light-sensitive silver halide emulsion layer and a non-diffusible dye-providing compound associated with this layer is exposed imagewise and developed with a silver halide developer, a diffusible dye being released imagewise from the non-diffusible dye-providing compound under alkaline photographic development conditions transferred to an image receptor layer, in which the non-diffusible dye providing compound used is a compound corresponding to the following formula I:

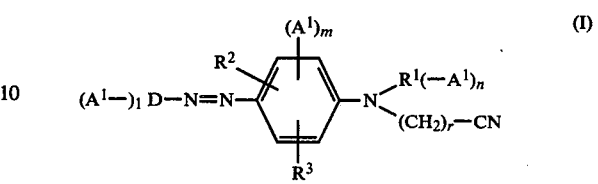

in which $A^1$ represents an oxidizable organic carrier residue containing a group which confers diffusion resistance, from which residue, either in its oxidized or in its unoxidized form, at least a part thereof together with the group which confers diffusion resistance is split off under alkaline photographic development conditions and at the same time a diffusible azo dye is released imagewise;

D represents a heterocyclic or carbocyclic aromatic group;

$R^1$ represents hydrogen or an alkyl, aralkyl or aryl group $R^2$ and $R^3$, which may be the same or different, each represents one of the groups mentioned under $R^1$, sulpho, $-COOR^4$, halogen, trihalogenmethyl, acylamino, acyloxy, carbamoyl, sulphamoyl, $-OR^4-$, $SR^4$, $-SOR^4$, $-SO_2-R^4$, in which $R^4$ has one of the meanings specified for $R^1$, $-NO_2$ or $-CN$;

l, m and n each represents 0 or 1 such that $l+m+n=1$; and r represents an integer of from 1 to 4.

2. The process as claimed in claim 1, in which the non-diffusible dye-providing compound used is a compound of the formula II:

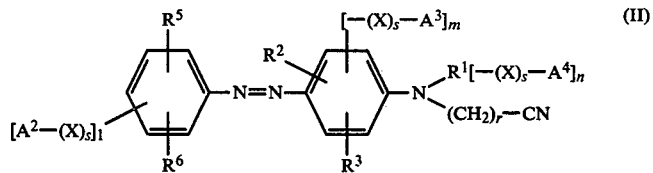

in which $A^2$ represents an oxidizable organic carrier residue in the o-, m- or p-position to the azo group, which carrier residue contains a group which confers diffusion resistance and which carrier residue may be attached through a connecting member X, from which carrier residue, either in its oxidized form or in its unoxidized form, at least part thereof together with the group which confers diffusion resistane is split off under alkaline photographic development conditions and a diffusible azo dye is at the same time released imagewise;

$A^3$ represents an oxidizable organic carrier residue containing a group which confers diffusion resistance and which carrier residue may be attached through a connecting member X, which carrier residue is attached in the ortho- or meta-position, either directly or through one of the substituents $R^2$ $R^3$, to the phenyl ring which carries the cyanoalkylamino group, from which carrier residue, either in the oxidized form or in the unoxidized form, at least part thereof together with the group which confers diffusion resistance is split off under alkaline photographic development conditions and at the same time a diffusible azo dye is released imagewise;

$A^4$ represents an oxidizable organic carrier residue which may be attached through a connecting member X and contains a group which confers diffusion resistance, which carrier residue is attached to the substituent $R^1$ and from which carrier residue, either in the oxidized form or in the unoxidized form, at least a part thereof together with the group which confers diffusion resistance is split off under alkaline photographic development conditions and a diffusible azo dye is at the same time released imagewise;

$R^1$ represents hydrogen or an alkyl, aralkyl or aryl group;

$R^2$, $R^3$, $R^5$ and $R^6$, which may be the same or different, each represents one of the groups mentioned under $R^1$, sulpho, —$COOR^4$, halogen, trihalogenmethyl, acylamino, acyloxy, carbamoyl, sulphamoyl, —$OR^4$, —$SR^4$, —$SOR^4$, —$SO_2$—$R^4$, wherein $R^4$ has one of the meanings specified for $R^1$, —$NO_2$ or —CN;

X represents a bivalent connecting member corresponding to the formula —R—$(L)_p$—$(R)_q$—, in which R represents an alkylene group or a substituted or unsubstituted phenylene group and the two groups R may be the same or different;

L represents —O—, —CO—, —$CONR^7$, —$SO_2NR^7$, —O—CO—$NR^7$, —S—, —$SO_2$— or —SO— in which $R^7$ = hydrogen or alkyl;

p = 0 or 1, q = 0 or 1, and q = 1 when p = 1 l, m and n each represents 0 or 1 such that l + m + n = 1;

r represents 2 or 3; and s represents 0 or 1.

3. The process as claimed in claim 1, in which the non-diffusible dye-providing compound used is a compound of the formula III:

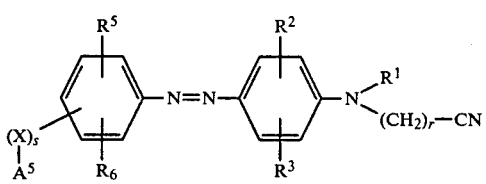

in which $R^1$ represents hydrogen or alkyl;

$R^2$, $R^3$, $R^5$ and $R^6$ which may be the same or different, represents hydrogen, chlorine, methyl, methoxy, acylamino, or nitro;

$A^5$ represents a group corresponding to one of the following formulae substituted with at least one group which confers diffusion resistance:

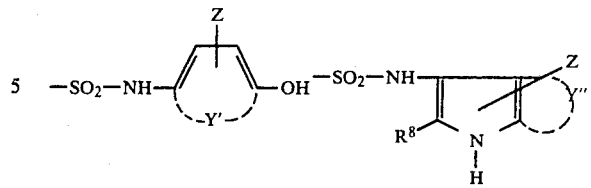

in which

Z represents a group which confers diffusion resistance;

Y' represents a group required to complete a benzene or naphthalene ring;

Y" represents a group required to complete a condensed, carbocyclic or heterocyclic ring, which may be substituted and $R^8$ represents hydrogen, or an alkyl, alkoxy, aryl heterocyclic, carboxyl, carbamoyl or alkoxycarbonyl group;

X represents a bivalent connecting member corresponding to the formula —R—$(L)_p$—$(R)_q$—, in which R represents an alkylene group or a substituted or unsubstituted phenylene group and the two groups R may be the same or different;

L represents —O—, —CO—, —$CONR^7$, —$SO_2NR^7$ —O—CO—$NR^7$ —S— —$SO_2$—or —SO— in which $R^7$ = hydrogen or alkyl;

p = 0 or 1;

q = 0 or 1; and q = 1 when p = 1;

r = 2 or 3 and;

s = 0 or 1.

4. The process as claimed in any of claims 1 to 3 in which $R^1$ represents an alkyl group which contains from 1 to 5 carbon atoms.

5. The process are claimed in claim 2 in which R represents an alkylene group which contains from 1 to 6 carbon atoms.

6. A photographic material useful in the process of claim 1, said material having at least one light-sensitive silver halide emulsion layer, said layer providing a diffusible dye releasable imagewise under alkaline photographic development conditions and transferrable to an image receptor layer, said silver halide emulsion layer containing a compound corresponding to the following formula I:

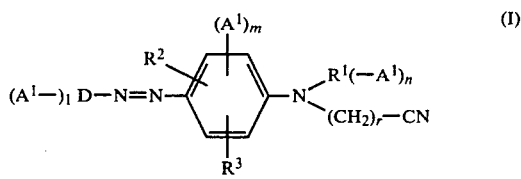

in which $A^1$ represents an oxidizable organic carrier residue containing a group which confers diffusion resistance, from which residue, either in its oxidized or in its unoxidized form, at least a part thereof together with the group which confers diffusion resistance is split off under alkaline photographic development conditions and at the same time a diffusible azo dye is released imagewise;

D represents a heterocyclic or carbocyclic aromatic group;

$R^1$ represents hydrogen or an alkyl, aralkyl or aryl group;

$R^2$ and $R^3$, which may be the same or different, each represents one of the groups mentioned under $R^1$, sulpho, —$COOR^4$, halogen, trihalogenmethyl, acylamino, acyloxy, carbamoyl, sulphamoyl, —$OR^4$—, $SR^4$, —$SOR^4$, —$SO_2R^4$, in which $R^4$ has one of the meanings specified for $R^1$, —$NO_2$ or —CN;

l, m and n each represents 0 or 1 such that $l+m+n=1$; and r represents an integer of from 1 to 4, said compound being non-diffusible and releasing said diffusible dye under said development conditions and said diffusible dye being transferrable to said receptor layer to produce an image.

* * * * *